(12) United States Patent
Zhang

(10) Patent No.: US 12,369,779 B2
(45) Date of Patent: Jul. 29, 2025

(54) ENDOSCOPE STRUCTURE

(71) Applicant: SCIVITA MEDICAL TECHNOLOGY CO., LTD., Suzhou (CN)

(72) Inventor: Yi Zhang, Suzhou (CN)

(73) Assignee: SCIVITA MEDICAL TECHNOLOGY CO., LTD., Suzhou (CN)

(*) Notice: Subject to any disclaimer, the term of this patent is extended or adjusted under 35 U.S.C. 154(b) by 275 days.

(21) Appl. No.: 17/778,021

(22) PCT Filed: Nov. 18, 2019

(86) PCT No.: PCT/CN2019/119202
§ 371 (c)(1),
(2) Date: May 19, 2022

(87) PCT Pub. No.: WO2021/097617
PCT Pub. Date: May 27, 2021

(65) Prior Publication Data
US 2023/0389779 A1 Dec. 7, 2023

(51) Int. Cl.
*A61B 1/005* (2006.01)
*A61B 1/00* (2006.01)

(52) U.S. Cl.
CPC .......... *A61B 1/005* (2013.01); *A61B 1/00066* (2013.01); *A61B 1/00071* (2013.01); *A61B 1/0052* (2013.01); *A61B 1/0057* (2013.01)

(58) Field of Classification Search
CPC ..... A61B 1/005; A61B 1/0052; A61B 1/0057; A61B 1/00066; A61B 1/00071; A61B 1/0055

(Continued)

(56) References Cited

U.S. PATENT DOCUMENTS 3,897,775 A * 8/1975 Furihata ............. A61B 1/00066
600/146
5,704,898 A * 1/1998 Kokish ................. A61B 34/71
600/152

(Continued)

FOREIGN PATENT DOCUMENTS

CN 107397525 A 11/2017
CN 108634920 A 10/2018

(Continued)

*Primary Examiner* — Aaron B Fairchild
(74) *Attorney, Agent, or Firm* — Bayramoglu Law Offices LLC

(57) ABSTRACT

The present invention relates to the field of medical devices, particularly an endoscope structure, which consists of a shell, an insertion section and a handheld section on the sides of the shell, the shell consists of a $1^{st}$ shell and a $2^{nd}$ shell spliced with each other, both the insertion section and the handheld section can rotate relatively to the shell, a scope tube is arranged inside the insertion section to insert into to-be-observed tissues, and an adjustment mechanism is arranged inside the shell to control the deflection of the scope tube. The beneficial effects of the present invention are: by arranging several plug-in structures and clamping structures between the $1^{st}$ shell and the $2^{nd}$ shell, the shell can be easily assembled; the insertion section and the handheld section are made into the structures that can rotate relatively to the shell, during use, rotation at angles according to actual needs can be realized, and the convenience can be increased for actual surgeries; by manually turning the adjustment handle from outside of the shell, the adjustment mechanism is driven to adjust the deflection direction of the scope tube, the practicability and convenience of the scope tube is greatly improved during tissue observation.

4 Claims, 11 Drawing Sheets

(58) Field of Classification Search
USPC .......................................................... 600/137
See application file for complete search history.

(56) References Cited

U.S. PATENT DOCUMENTS

2005/0054899 A1* 3/2005 Miyake ................ A61B 1/0052
                                                      600/152
2017/0238787 A1* 8/2017 Hijihara ............... A61B 1/0052

FOREIGN PATENT DOCUMENTS

| CN | 109316158 A   | 2/2019  |
|----|---------------|---------|
| CN | 110123245 Y   | 8/2019  |
| CN | 209595701     | 11/2019 |
| CN | 209595705     | 11/2019 |
| CN | 209595715 Y   | 11/2019 |
| CN | 209595716 Y   | 11/2019 |

* cited by examiner

ENDOSCOPE STRUCTURE

TECHNICAL FIELD

The present invention relates to the field of medical devices, particularly an endoscope structure.

BACKGROUND TECHNOLOGY

With the development of technologies, more and more instruments are used in modern surgeries, surgical instruments can well help doctors to perform surgeries and greatly improve the convenience and safety. For urological surgeries, interventional treatments are required for removing kidney stones, generally, breaking kidney stones with extracorporeal shock wave lithotripsy (ESWL), nephrolithotomy and percutaneous nephrolithotomy are adopted. Therefore, endoscope is often used together with instruments to perform such surgeries.

It is found through patent search that, a published patent under No. CN107374570A discloses an electronic software-based ureteropelvic endoscopy, which consists of an insertion head, a bendable tube, an operation handle, a $1^{st}$ traction wire, a $2^{nd}$ traction wire and a rotating arm; among which, connection rods are respectively arranged on the ends of the rotating arm, guide parts are arranged on one ends of the connection rods away from the rotating arm, 2 guide grooves are arranged on the operation handle, the guide parts slide and are arranged inside the guide grooves, the $1^{st}$ traction wire and the $2^{nd}$ traction wire are respectively fixed onto the guide parts, and a rotating paddle is arranged on the operation handle to adjust the rotating arm.

An electronic software-based ureteropelvic endoscopy disclosed in the above technical scheme, by rotating the rotating arm, it adjusts the positions of the guide parts inside the guide grooves on both sides, realizes the alternating expansion and contraction between the $1^{st}$ traction wire and the $2^{nd}$ traction wire, adjusts the angle of the insertion angle can be adjusted, and makes it convenient for staff to observe. However, it has many small parts not conducive to assembling.

SUMMARY

The objective of the present invention is to design an endoscope structure to solve above issues.

The technical scheme defined in the present invention to achieve above objective is, an endoscope structure, which consists of a shell, an insertion section and a handheld section on the sides of the shell, the shell consists of a $1^{st}$ shell and a $2^{nd}$ shell spliced with each other, both the insertion section and the handheld section can rotate relatively to the shell, a scope tube is arranged inside the insertion section to insert into to-be-observed tissues, and an adjustment mechanism is arranged inside the shell to control the deflection of the scope tube.

Among which, the $1^{st}$ shell and the $2^{nd}$ shell are connected through several plug-in structures or clamping structures.

A feasible embodiment of the connection structure between the $1^{st}$ shell and the $2^{nd}$ shell: the connection structure consists of several positioning pins arranged on the $1^{st}$ shell and several positioning grooves correspondingly arranged on the $2^{nd}$ shell, and the positioning pins can be inserted into the positioning grooves; the clamping structure consists of an inner lining edge arranged in the $1^{st}$ shell and an outer lining edge arranged in the $2^{nd}$ shell, both the inner lining edge and the outer lining edge are of a ladder shape, and they can embrace each other.

The mode of connection between the insertion section and the shell: a rotating head is arranged at the position where the insertion section contacts with the shell, a connecting hole corresponding to the rotating head is arranged on the shell, the rotating head and the connecting hole are clamped and connected, they can and can only rotate relatively to each other.

Further, a ring groove is arranged on the rotating head, a pit is fixed inside the ring groove, a bump is fixed inside the connecting hole, when the rotating head rotates, the pit and the bump contact with each other and limit the rotation range of the rotating head.

A feasible embodiment of the adjustment mechanism: the adjustment mechanism consists of a pulley arranged inside the shell and can rotate along the axis of the shell, a handle used to control the rotation of the pulley from outside of the shell, and traction wires stretching along one side of the pulley to the scope tube, among which, the number of the traction wires are 2, and the two traction wires respectively pass through the sides of the pulley and reach the scope tube.

Specific structure of the runner: a limit mechanism is arranged on the end surface of the pulley to fix the traction wires, a guide groove is arranged on the lateral annular wall of the runner, the traction wires stretch from the limit mechanism, pass through the guide groove and connect with the scope tube.

Specific scheme of the limit mechanism: the limit mechanism consists of a fixing groove arranged on the end surface of the limit mechanism, a limit block and a fixed block arranged inside the fixing groove, one ends of the traction wires pass through the limit block and fixedly connect with the fixed block.

As an optional embodiment of the adjustment mechanism, the adjustment mechanism also consists of a backing plate arranged outside the end surface of the pulley to cover the limit mechanism, and the backing plate is fixed onto the end surface of the pulley with a screw.

As another optional embodiment of the adjustment mechanism, the adjustment mechanism also consists of a guide plate arranged on the inner wall of the shell, the guide plate is between the pulley and the scope tube, and a limit groove corresponding to the traction wires is arranged on the guide plate to limit the placement position of the traction wires.

The beneficial effects are, 1. By arranging several plug-in structures and clamping structures between the $1^{st}$ shell and the $2^{nd}$ shell, the shell can be easily assembled. When the $1^{st}$ shell and the $2^{nd}$ shell need to be buckled together, just align the positioning pins with the positions of the positioning grooves, align the inner lining edge with the position of the outer lining edge, then press and combine to easily buckle the two shells together.

The insertion section and the handheld section are made into the structures that can rotate relatively to the shell, during use, rotation at angles according to actual needs can be realized, and the convenience can be increased for actual surgeries. Since the ring groove is arranged on the rotating head in the insertion section, and the ring groove cooperates with the connecting hole, so when rotation is needed, only need to rotate the insertion section or the handheld section, without affecting the rotation of the shell or the overall operation stability, the convenience is provided for surgeries.

By manually turning the adjustment handle from outside of the shell, the adjustment mechanism is driven to adjust the deflection direction of the scope tube, the practicability and convenience of the scope tube is greatly improved during tissue observation. By pulling the two traction wires, the deflection of the scope tube can be controlled, one ends of the traction wires are fixed inside the fixing groove, such ends of the traction wires then pass through the guide groove and the guide plate, enter the scope tube in the insertion section; by rotating the adjustment mechanism, the tightness of the traction wires can be changed, combing the rotation of the insertion section relative to the shell, the deflection of the scope tube in all directions can be realized.

DESCRIPTION OF EMBODIMENTS

In figures, 1. Shell; 101. $1^{st}$ shell; 102. $2^{nd}$ shell; 103. Positioning pin; 104. Positioning groove; 105. Inner lining edge; 106. Outer lining edge; 2. Insertion section; 201. Rotating head; 202. Connecting hole; 203. Ring groove. 204. Pit; 205. Bump; 3. Handheld section; 4. Adjustment mechanism; 401. Runner; 402. Handle; 403. Traction wire; 404. Scope tube; 405. Guide groove; 406. Guide plate; 407. Limit groove; 408. Fixing groove; 409. Limit groove; 410. Fixed block; 411. Backing plate.

DESCRIPTION OF EMBODIMENTS

The structure defined in the present invention applies to all the products in related similar application fields, in order to enable those skilled in the art to understand the structure of the present invention, a specific embodiment is described below, the embodiment described below is a medical endoscope, particularly a medical endoscope for kidney tissue observation. As a common knowledge to those skilled in the art, the renal endoscope consists of a shell 1, an insertion section 2 and a handheld section 3 on the sides of the shell 1; during actual use, the insertion section 2 is inserted into the to-be-observed tissues inside the patient, the handheld section 3 is held by the medical staff, the tail of the handheld section 3 is connected with the video data wire, the images inside the tissues are transmitted through the micro camera arranged inside the head of the insertion section 2 to the external display device for medical staff to observe the patient's tissues and determine treatment or surgery.

This embodiment is described and explained below by combing FIGS. 1-11 from three parts, the three parts are the buckling structure of the shell 1, the structure in which the insertion section 2 and the handheld section 3 rotate relatively to the shell 1, and the specific structure of the adjustment mechanism 4.

Figure 5:
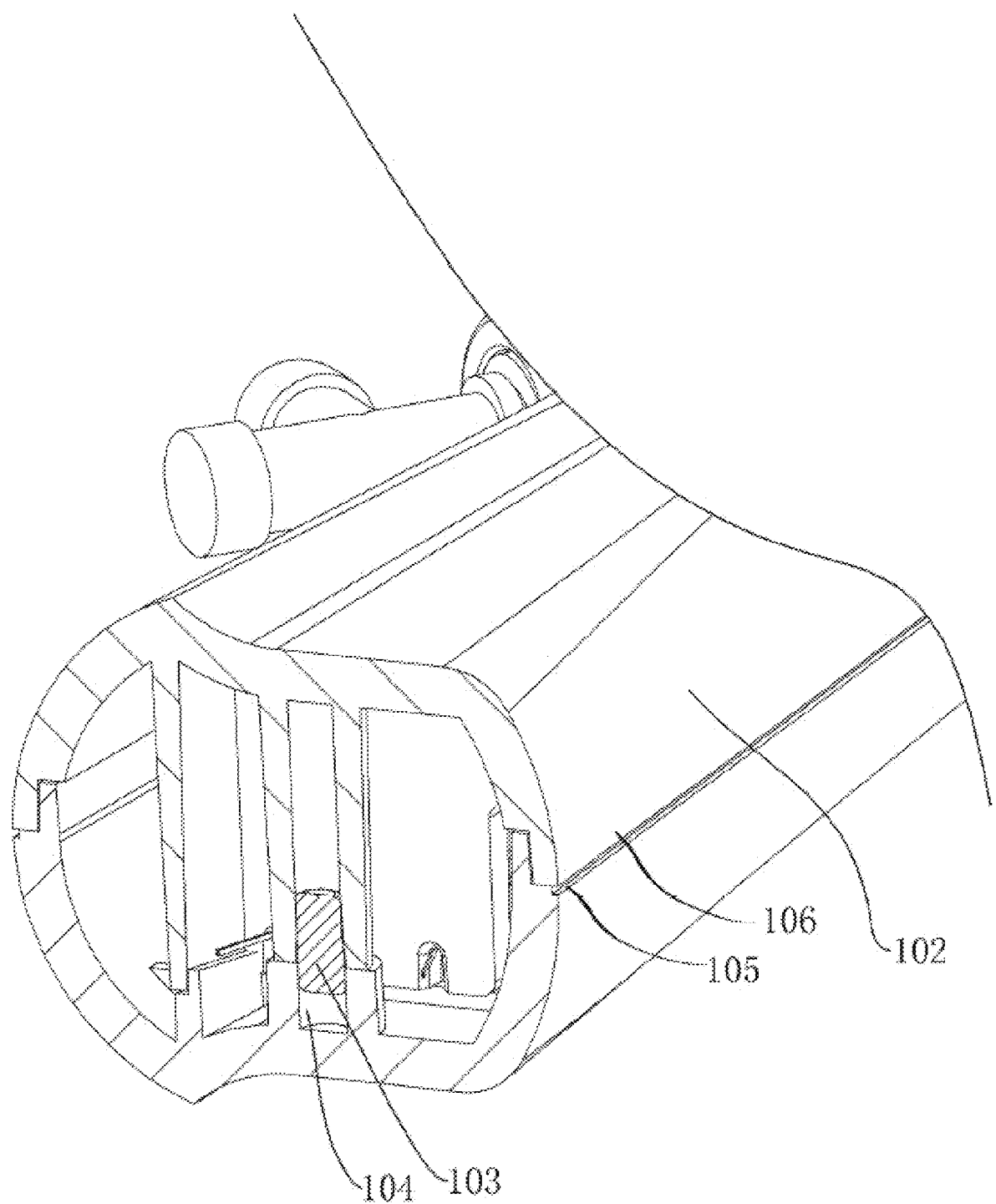
FIG. 5 is a cross-sectional view of the buckling structure of the two shells of the present invention.
Figure 6:
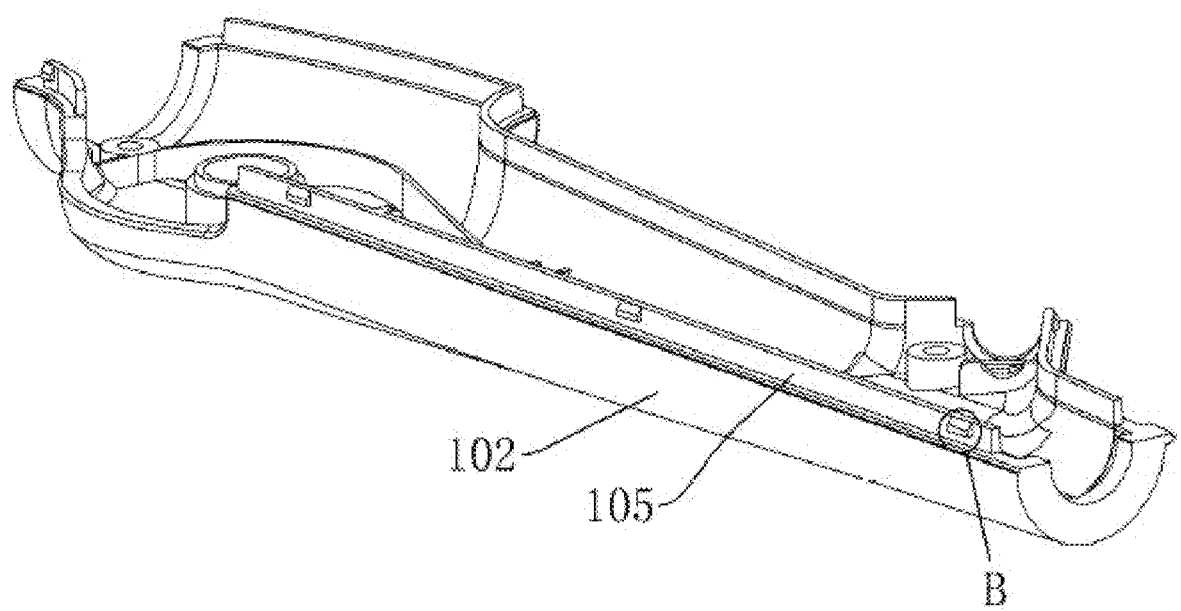
FIG. 6 is a structural view of the inner lining edge of the $2^{nd}$ shell of the present invention.
Figure 7:
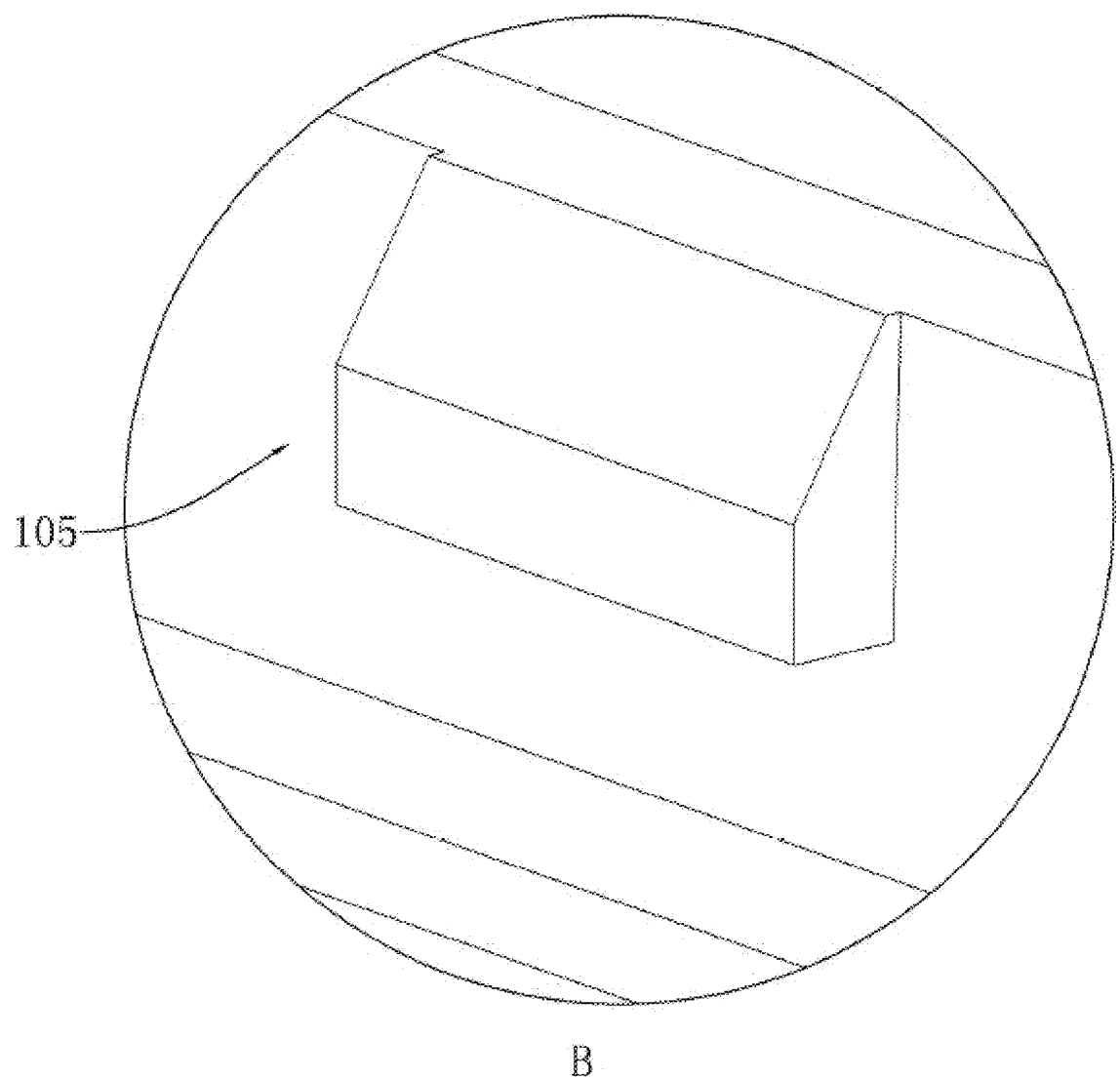
FIG. 7 is an enlarged view of Structure B as shown in FIG. 6.
Figure 8:
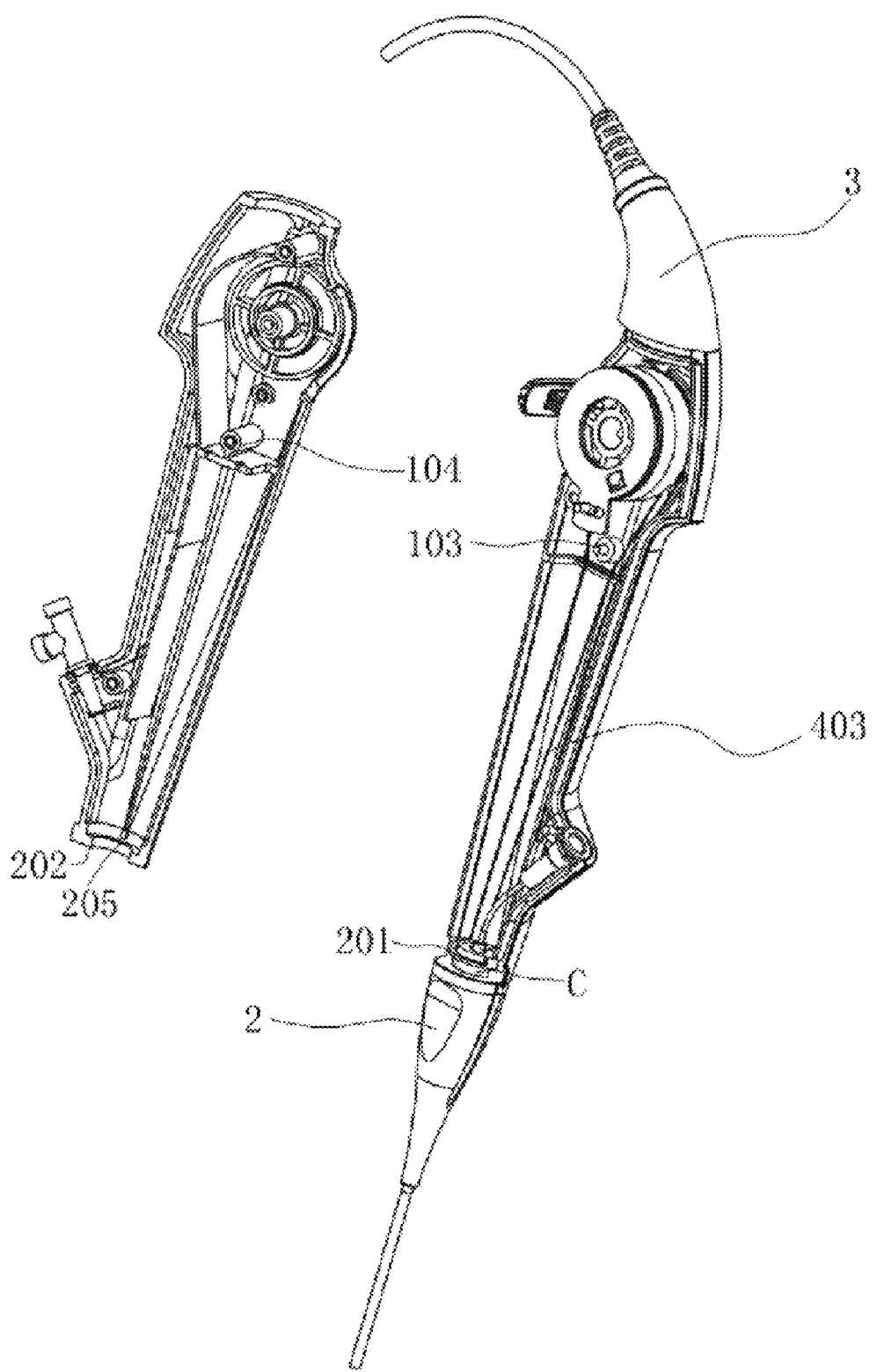
FIG. 8 is an exploded view of the overall split present invention.
Figure 9:
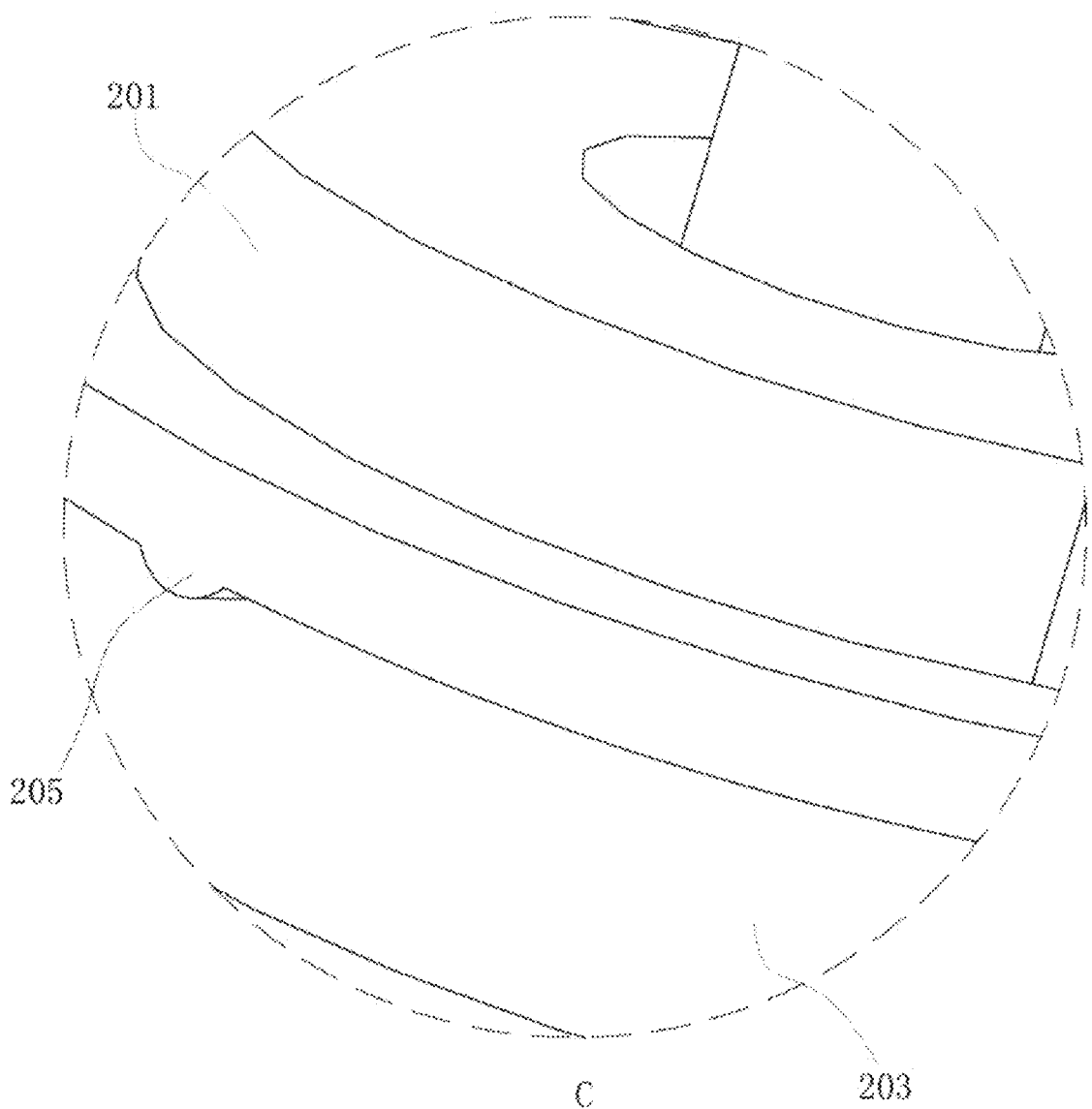
FIG. 9 is an enlarged view of Structure C as shown in FIG. 8.
Figure 10:
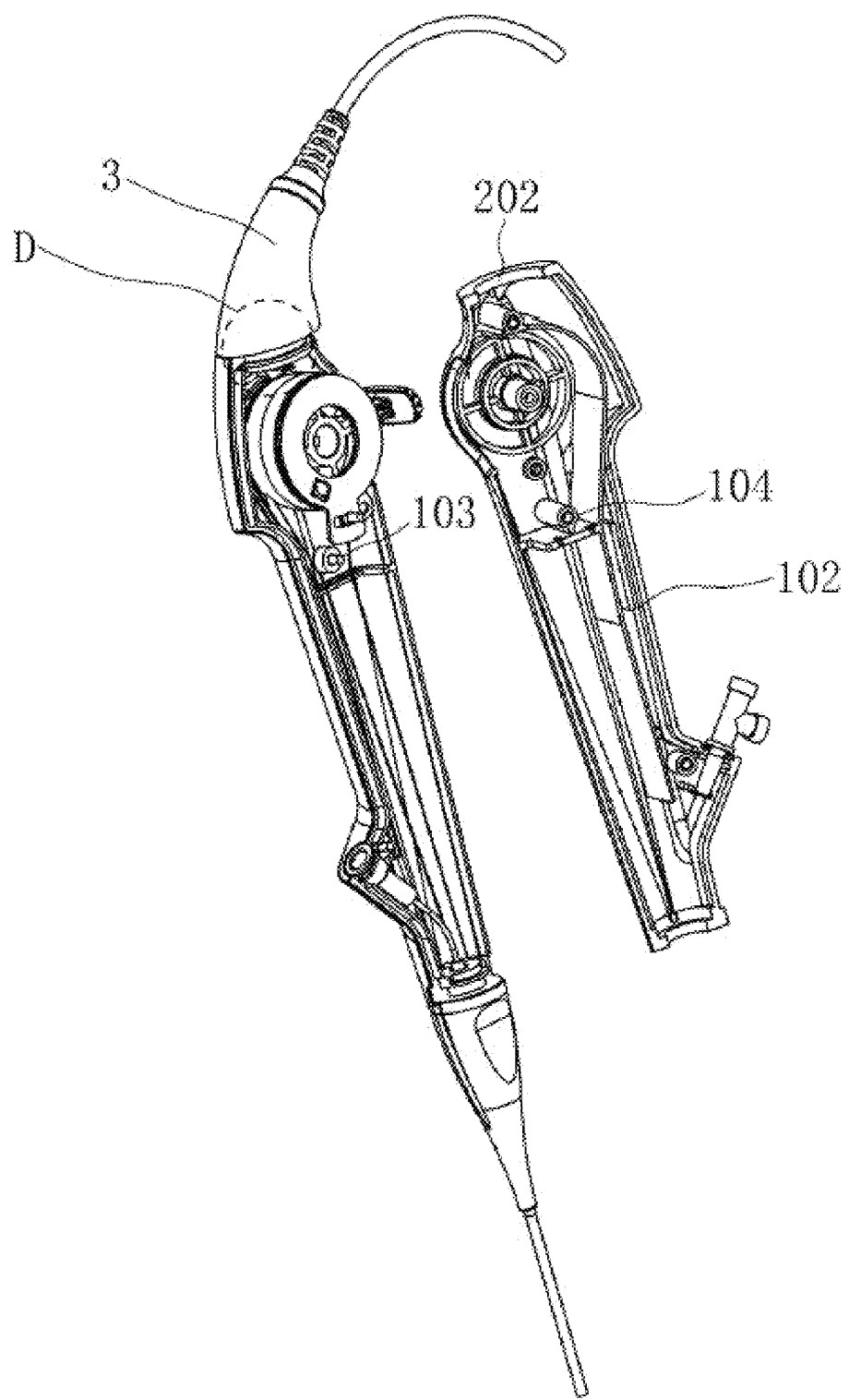
FIG. 10 is a structural split view from another angle of the present invention.
Figure 11:
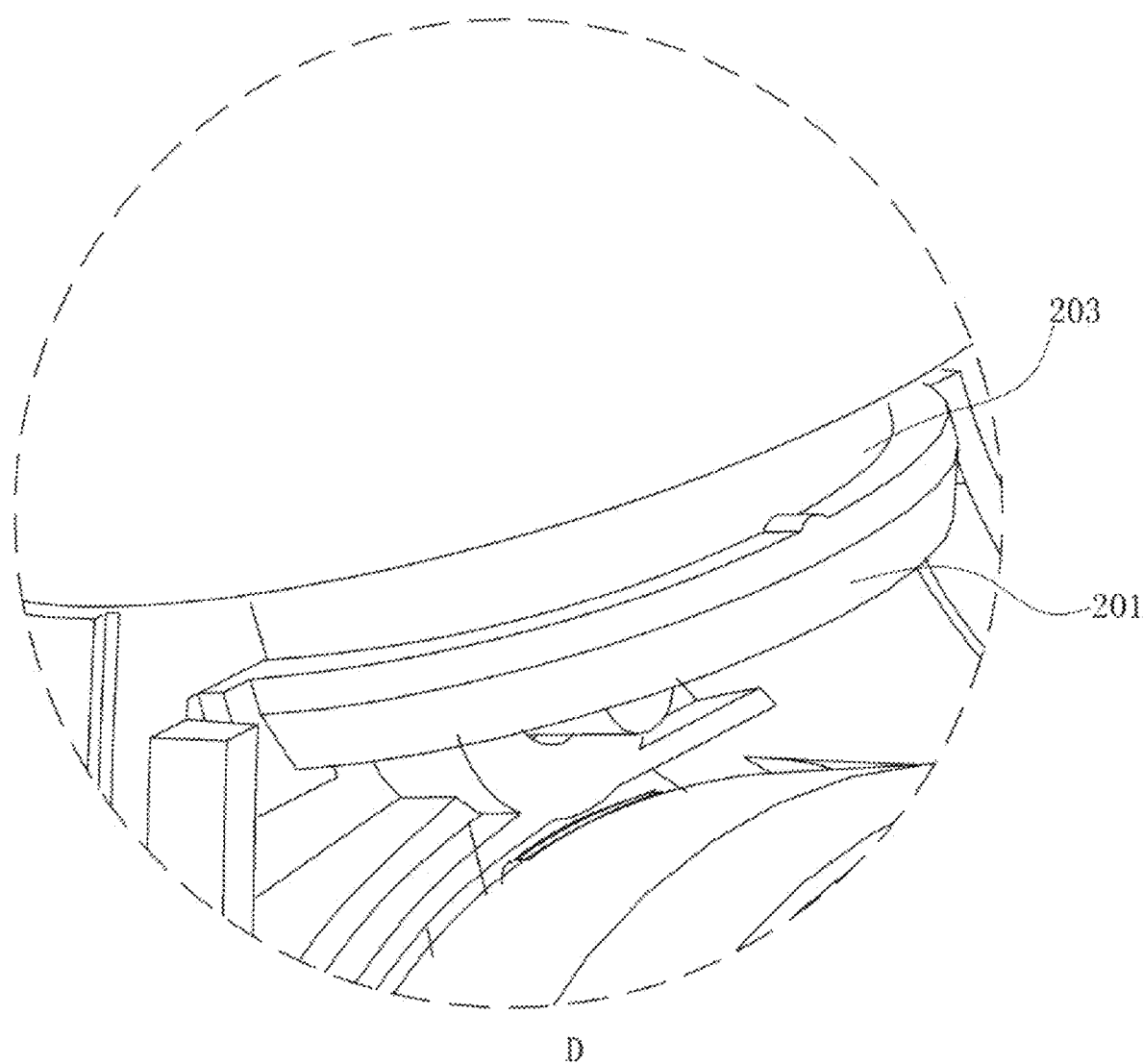
FIG. 11 is an enlarged view of Structure D as shown in FIG. 10.

Firstly, the buckling structure of the shell 1 in the present invention is described below by combing FIG. 5"7: For this embodiment, the shell 1 consists of the $1^{st}$ shell and the $2^{nd}$ shell, in order to firmly clamp and connect the two shells and make assembling and disassembling convenient, the positioning pins 103 are fixed on the inner wall of the $1^{st}$ shell 101, and the positioning grooves 104 corresponding to the positioning pins 103 are arranged on the inner wall of the $2^{nd}$ shell 102, the positioning pins 103 can be inserted into the positioning grooves 104 to connect the shell 1; however, it shall be considered that, the structure between the positioning pins 103 and the positioning grooves 104 may limit the movement of the shell 1 on their joint surface, but since the vertical distance is long, when the two shells of the shell 1 slide relatively to each other, the positioning pins 103 and the positioning grooves 104 may get loose or break, therefore, in order to avoid the above result, a lining edge structure needs to be arranged on the basis of the buckling structure, that is, the inner lining edge 105 is arranged inside the $1^{st}$ shell 101, the outer lining edge 106 is arranged inside the $2^{nd}$ shell 102, through the cooperation between the inner lining edge 105 and the outer lining edge 106, the firm connection between the two shells of the shell 1 can be enhanced, and getting loose or breaking of the positioning pins 103 and the positioning grooves 104 resulted from the two shells of the shell 1 sliding relatively to each other can be prevented.

Secondly, the structure in which the insertion section 2 and the handheld section 3 rotate relatively to the shell 1 in the present invention is described below by combing FIG. 8~11: For this embodiment, the rotating head 201 is arranged at the position where the insertion section 2 contacts with the shell 1, the connecting hole 202 is arranged on the shell 1, and the rotating head 201 is inserted into the connecting hole 202. In order to realize the rotation of the insertion section 2 relative to the shell 1, the ring groove 203 is arranged on the rotating head 201, and it is required that the outer diameter of the ring groove 203 shall be 0.5 mm 1 mm smaller than the inner diameter of the connecting hole 202, and that the outer diameter of the rotating head 201 shall be bigger than the inner diameter of the connecting hole 202; once the rotating head 201 is inserted into the connecting hole 202, there will be only rotational degree of freedom for the insertion section 2 relative to the shell 1, that is, the insertion section 2 can only rotate relatively to the shell 1 along their contacting surface, the requirement of the insertion section 2 rotating relatively to the shell 1 can be met; however, it can be found during actual use that, since the insertion section 2 also needs to cooperate with other structures (such as cooperating with the traction wires 403 to control the deflection of the scope tube 404), if the insertion section 2 rotates more than 180°, the two traction wires 403 may intertwine, the deflection of the scope tube 404 can't be normally controlled, therefore, the rotation angle of the rotating head 201 must be limited; for this purpose, the pit 204 is fixed inside the ring groove 203, the bump 205 is fixed inside the connecting hole 202, during the rotation of the rotating head 201, the pit 204 and the bump 205 contact with each, stop the rotating head 201 from continuous rotating, limit the rotation range of the rotating head 201, and prevent the intertwining of the traction wires 403 due to big rotation angle of the insertion section 2. It shall be noted that, the connection mode between the handheld section 3 and the shell 1 are the same as the insertion section 2.

Thirdly, the specific structure of the adjustment mechanism 4 in the present invention is described below by combing FIG. 124: The major parts of the adjustment mechanism 4 include the pulley 401 arranged inside the shell 1 and can rotate along the axis of the shell 1, the handle 402 used to control the rotation of the pulley 401 by personnel from outside of the shell 1, and the two traction wires 403 stretching along one side of the pulley 401 to the scope tube 404, among which, the two traction wires 403 respectively pass through the sides of the pulley 401 and are fixed at the distal end of the pulley 401; the medical staff holds the present invention and turns the handle 402, the handle 402 drives the pulley 401 to rotate, the rotation of the pulley 401 drives the traction wires 403 to stretch, when the traction wires 403 are pulled, the traction wires 403 get tightened, when the traction wires 403 are released, the traction wires 403 get loose, when the pulley 401 rotates, one of the two traction wires 403 gets tightened, and the other gets loose, under the driving by the traction wires 403, the scope tube 404 deflects toward the direction of the tightened traction wire 403, and by the same way, the deflection of the insertion section 2 is controlled through the pulley 401.

Figure 1:
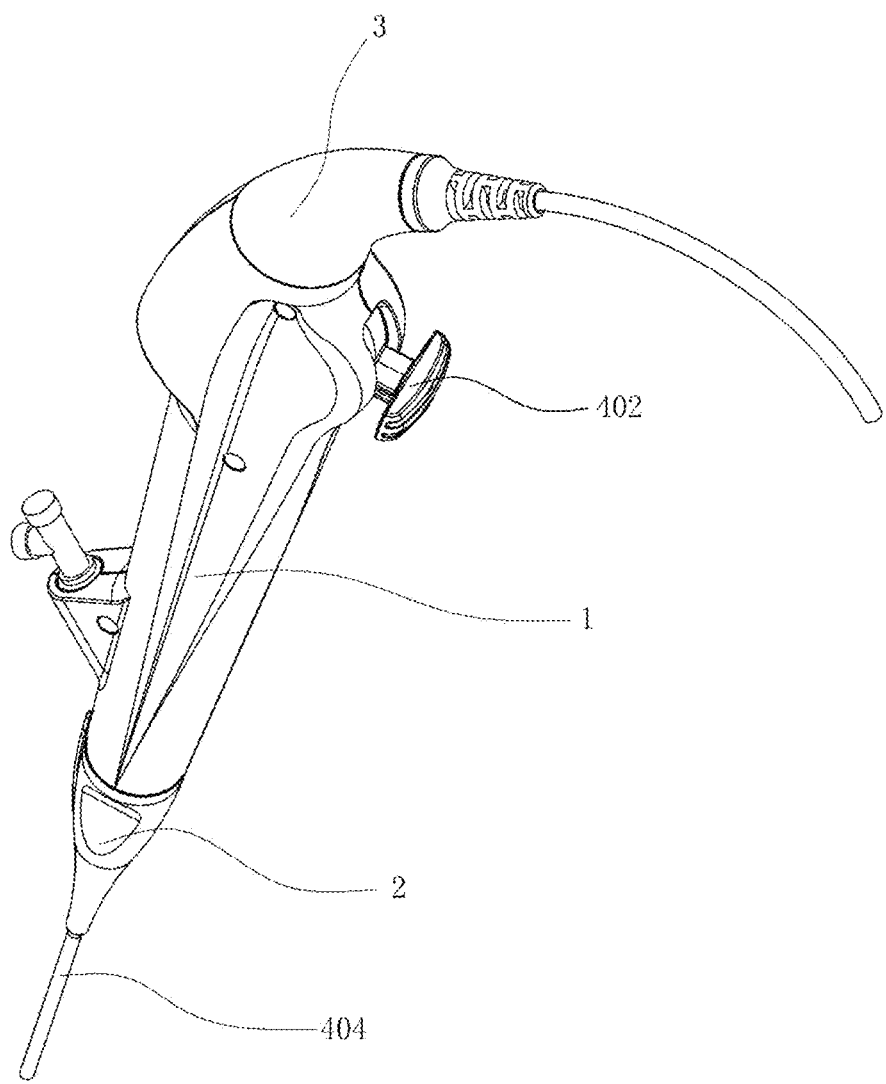
FIG. 1 is a view of the external structure of the present invention.
Figure 2:
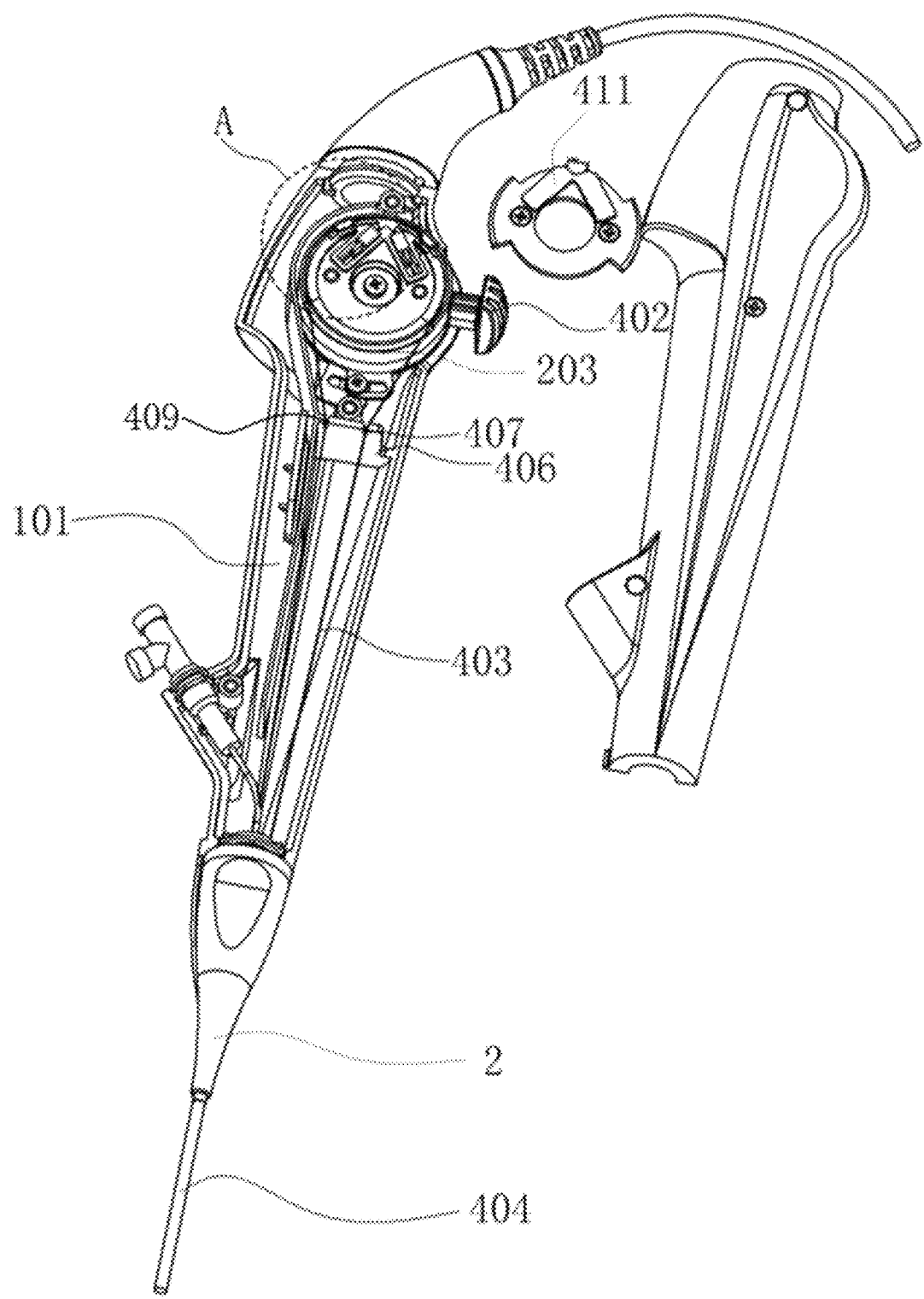
FIG. 2 is a structural view of the split $2^{nd}$ shell of the present invention.
Figure 3:
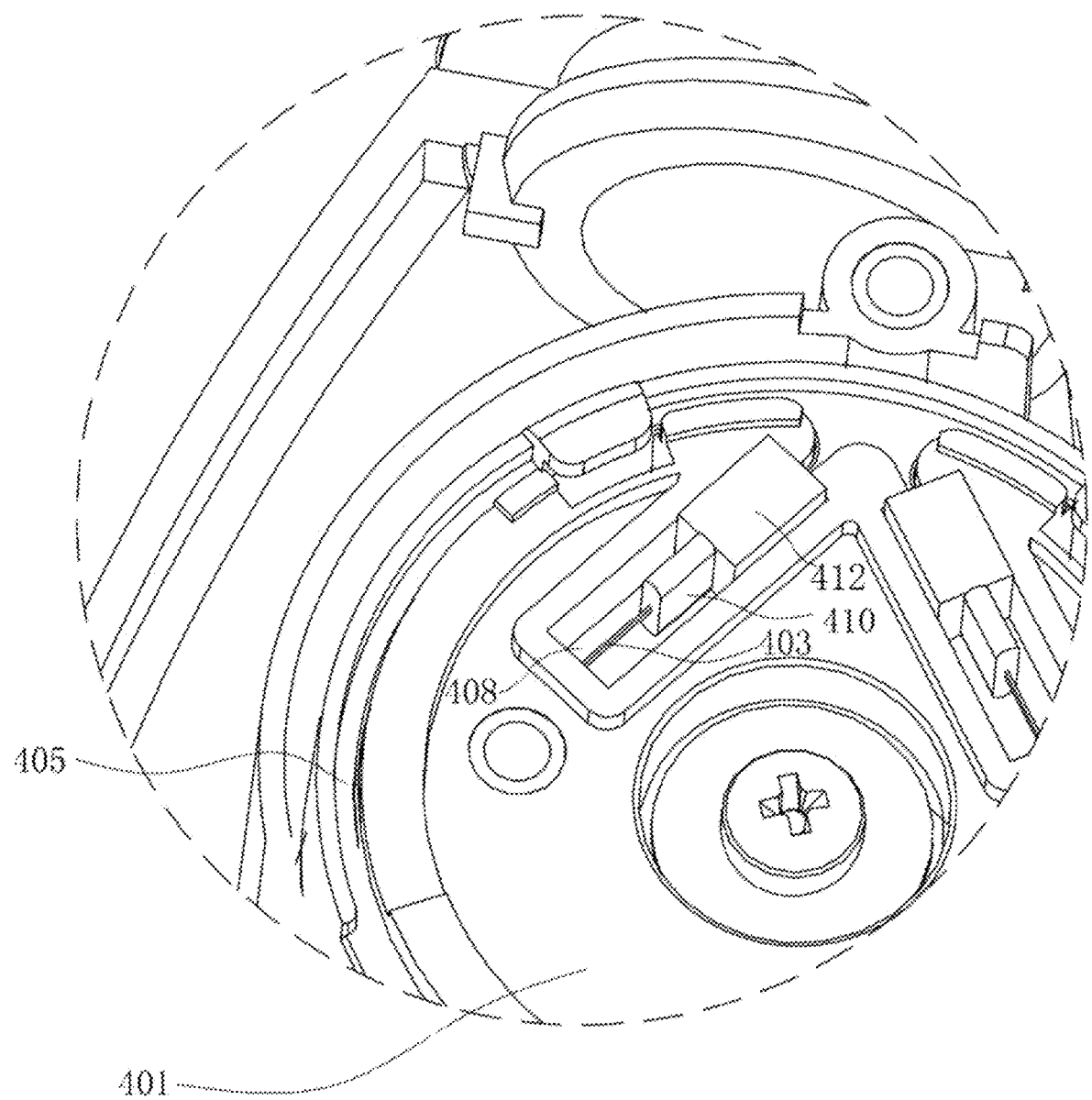
FIG. 3 is an enlarged view of Structure A as shown in FIG. 2.
Figure 4:
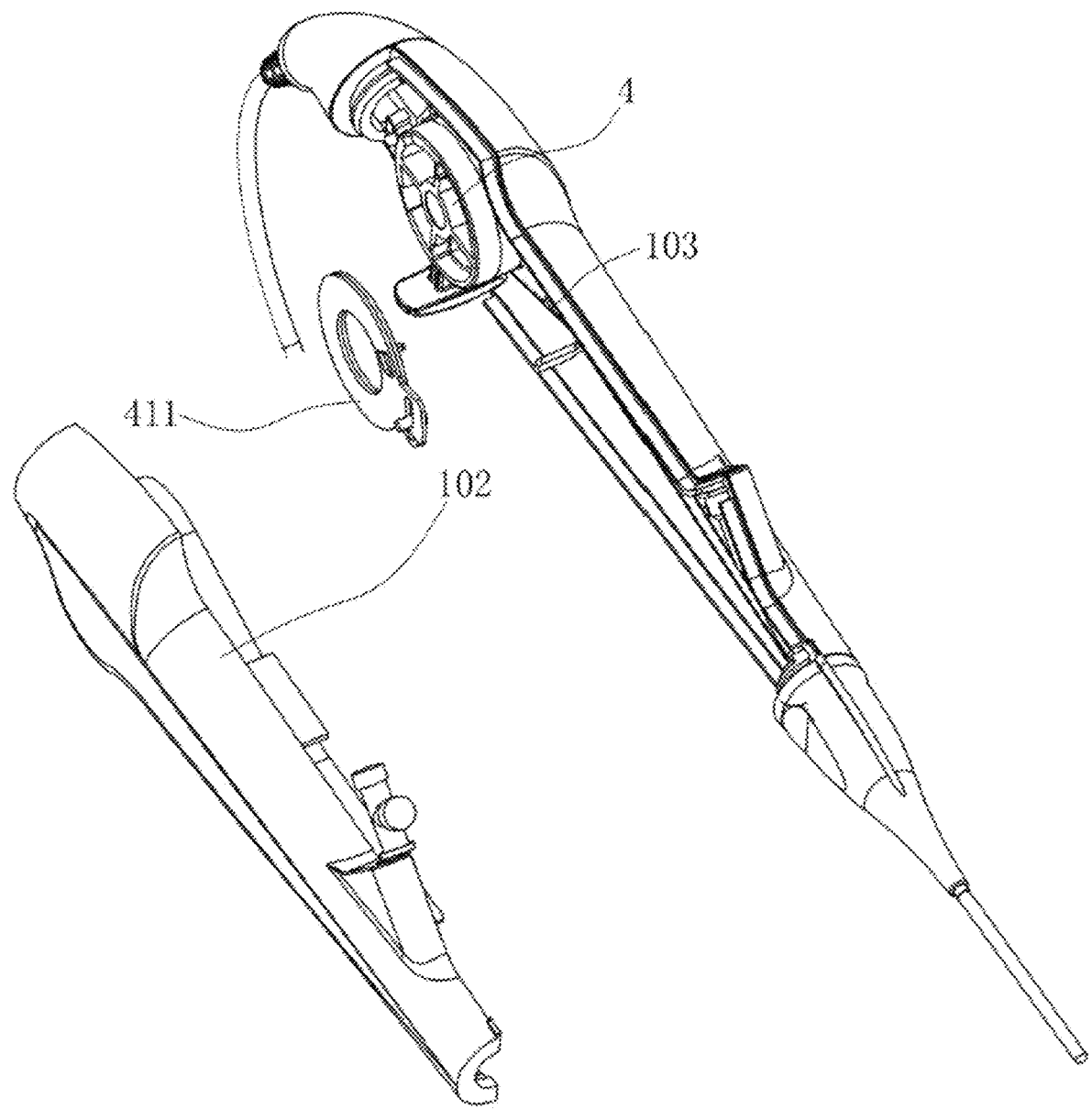
FIG. 4 is a view of the split structure of the present invention.

In order to better control the traction wires 403, the limit mechanism is arranged on the end surface of the pulley 401, the guide groove 405 is arranged on the lateral wall of the pulley 401 to limit the positions of the traction wires 403, the guide plate 406 is arranged on the inner wall of the shell 1, and limit grooves 409 and 407 are arranged; the limit mechanism consists of the fixing groove 408 arranged on the end surface of the pulley 401, the limit block 412 and the fixed block 410 arranged inside the fixing groove 408; by fixing the traction wires 403 onto the fixed block 410, blocking with the limit block 412, that is, one ends of the traction wires 403 are fixed inside the fixing groove 408, pass through the guide groove 405 and the limit grooves 409 and 407, then enter the scope tube 404, the design of the limit mechanism, the guide groove 405 and the guide plate 406 can limit the positions of the traction wires 403, and prevent falling of the traction wires 403 during rotation; in addition, in order to better protect the limit mechanism and prevent falling of the fixed block 410 and the limit block 412 arranged inside the limit mechanism, as shown in FIGS. 2 and 4, the backing plate 411 is arranged outside the pulley 401 to cover the limit mechanism, and the backing plate 411 is fixed onto the end surface of the pulley 401 with a screw.

The above technical scheme only reflects the preferred technical scheme of the technical scheme of the present invention, the changes in certain aspects of the technical scheme made by those skilled in the art reflect the principle of the present invention and fall into the protection scope of the present invention.

What is claimed is:

1. An endoscope comprising:
a shell having a first end and a second end,
an insertion section arranged on the first end of the shell and rotatable relative to the shell,
a handheld section, arranged on the second end of the shell and rotatable relative to the shell,
a scope tube arranged inside the insertion section and configured to be inserted into tissues to be observed, and
an adjustment mechanism arranged inside the shell and configured to control a deflection of the scope tube,
wherein the adjustment mechanism comprises:
a pulley arranged inside the shell and rotatable along an axis of the shell,
a handle configured to rotate the pulley from outside of the shell, and
two traction wires stretching along one side of the pulley to the scope tube,
and being configured to pass through the one side of the pulley and reach the scope tube,
wherein a limit mechanism is arranged on an end surface of the pulley to fix the two traction wires, a guide groove is arranged on a lateral annular wall of the pulley, and the two traction wires stretch from the limit mechanism, pass through the guide groove and connect to the scope tube.

2. The endoscope of claim 1, wherein,
the limit mechanism comprises a fixing groove arranged on an end surface of the limit mechanism,
a limit block and a fixing block are arranged inside the fixing groove, and
the two traction wires pass through the limit block and fixedly connect to the fixing block.

3. The endoscope of claim 1, wherein,
the adjustment mechanism further comprises a backing plate, the backing plate is arranged outside the end surface of the pulley to cover the limit mechanism, and the backing plate is fixed onto the end surface of the pulley with a screw.

4. The endoscope of claim 1, wherein,
the adjustment mechanism further comprises a guide plate arranged on an inner wall of the shell, the guide plate is positioned between the pulley and the scope tube, and
a limit groove corresponding to the two traction wires is arranged on the guide plate to limit a placement position of the two traction wires.

\* \* \* \* \*